US006867393B1

(12) United States Patent
Lewis (10) Patent No.: US 6,867,393 B1
(45) Date of Patent: Mar. 15, 2005

(54) STEAM STERILIZATION SYSTEM FOR STERILIZING MEDICAL WASTE

(76) Inventor: Robert W. Lewis, 9811 Warwick Cir., Charlotte, NC (US) 28210

( * ) Notice: Subject to any disclaimer, the term of this patent is extended or adjusted under 35 U.S.C. 154(b) by 0 days.

(21) Appl. No.: 10/728,467

(22) Filed: Dec. 5, 2003

(51) Int. Cl.$^7$ ............................ A61L 2/07; A61L 11/00; F27B 5/12; F27B 5/16; F27D 3/06
(52) U.S. Cl. ......................... 219/401; 422/26; 422/300; 422/307
(58) Field of Search ................................ 219/400, 401; 422/26, 243, 297, 300, 307

(56) References Cited

U.S. PATENT DOCUMENTS

| | | | | |
|---|---|---|---|---|
| 1,409,286 A | * | 3/1922 | Diner | 422/307 |
| 3,994,684 A | * | 11/1976 | Tomasulo | 422/297 |
| 4,170,421 A | * | 10/1979 | Balding et al. | 422/297 |
| 4,670,227 A | * | 6/1987 | Smith | 422/297 |
| 5,424,033 A | * | 6/1995 | Roland | 422/26 |
| 6,139,793 A | * | 10/2000 | Vanderwal | 422/307 |
| 6,348,174 B1 | * | 2/2002 | Hall | 422/26 |

* cited by examiner

Primary Examiner—Joseph Pelham
(74) Attorney, Agent, or Firm—John F. A. Earley, III; John F. A. Earley; Harding, Earley, Follmer & Frailey (57) ABSTRACT

A steam sterilization system for sterilizing medical waste comprises a cart for carrying a removable bin for holding medical waste, and a sterilization chamber that receives the bin when it is removed from the cart. The cart has wheels mounted thereon to provide mobility to the cart, and the cart has a rail assembly positioned at each side end portion. The bin for holding medical waste the bin being removably mountable to the cart, and the bin has wheels mounted on each side wall of the bin and spaced such that the wheels engage the rail assemblies of the cart when the bin is being loaded onto the cart and such that the wheels engage the rail assemblies of the cart when the bin is being removed from the cart. The sterilization chamber has a rail assembly mounted in the interior of the chamber on which the wheels of the bin ride when the bin is inserted into the chamber from the cart prior to sterilization and on which the wheels of the bin ride when the bin is being removed from the chamber and rolled back onto the cart after sterilization. A steam valve is connected to the chamber for introducing steam when desired into the chamber, and a vacuum pump is connected to the chamber for evacuating air in the chamber when desired.

17 Claims, 9 Drawing Sheets

STEAM STERILIZATION SYSTEM FOR STERILIZING MEDICAL WASTE

BACKGROUND OF THE INVENTION

1. Field of the Invention

This invention relates to a steam sterilization system for sterilization of items such as regulated medical waste, and more particularly concerns a steam sterilization system that integrates material handling with the sterilization process to reduce handling and pathogen exposure.

2. Description of the Prior Art

Regulated medical waste generated by hospitals and the like is required to be sterilized prior to being disposed. Typically, plastic and/or rubber carts of approximately one cubic yard in size are used in hospitals to collect medical waste which has been placed in waste containment systems (i.e., sharps containers, sealed red plastic bags, etc.). The plastic/rubber carts are used to collect and to haul the containmment systems containing the medical waste to the hospital's sterilization unit, where the waste containment systems containing the medical waste are unloaded from the cart and placed into the sterilization unit to be sterilized. After sterilization, the waste containment systems containing the now sterilized medical waste are transferred back onto the cart and conveyed to typically a solid waste compactor unit for final disposal, generally, in a sanitary landfill.

Sterilization units that are based upon steam sterilization generally have a drawback of water condensation from the steam forming on the treated medical waste, which increases the weight of the treated medical waste and therefore the cost of the disposing of the treated medical waste in a landfill.

Sterilization units based upon a vacuum autoclave have the drawback of potentially pumping airborne pathogens out of the vacuum autoclave into the environment during a sterilization process. This leads to potential contamination or alternatively to higher costs in providing filtration systems/ventilators for treating the airborne pathogens being pumped out of the vacuum autoclave.

SUMMARY OF THE INVENTION

It is an object of the invention to provide a sterilization system for sterilizing items such as regulated medical waste.

Another object of the invention is to provide a sterilization system that avoids the condensation drawback of known steam based sterilization units as well as the airborne pathogen drawback of known vacuum autoclave systems.

Another object of the invention is to provide a sterilization system that provides the efficacy of a vacuum based sterilization system without the airborne pathogen drawback mentioned above.

Still another object of the invention is to provide a sterilization system that integrates material handling with the sterilization process, thereby reducing handling and pathogen exposure.

These and other objects are accomplished by my invention which is set out below.

DETAILED DESCRIPTION

Turning to the drawings, there is shown a steam sterilization system 11 for sterilizing medical waste. In this preferred embodiment of the invention, the steam sterilization system 11 comprises a cart 13, a bin 15 for holding medical waste, the bin 15 being removably mountable to the cart 13, and a sterilization chamber 17.

Figure 8:
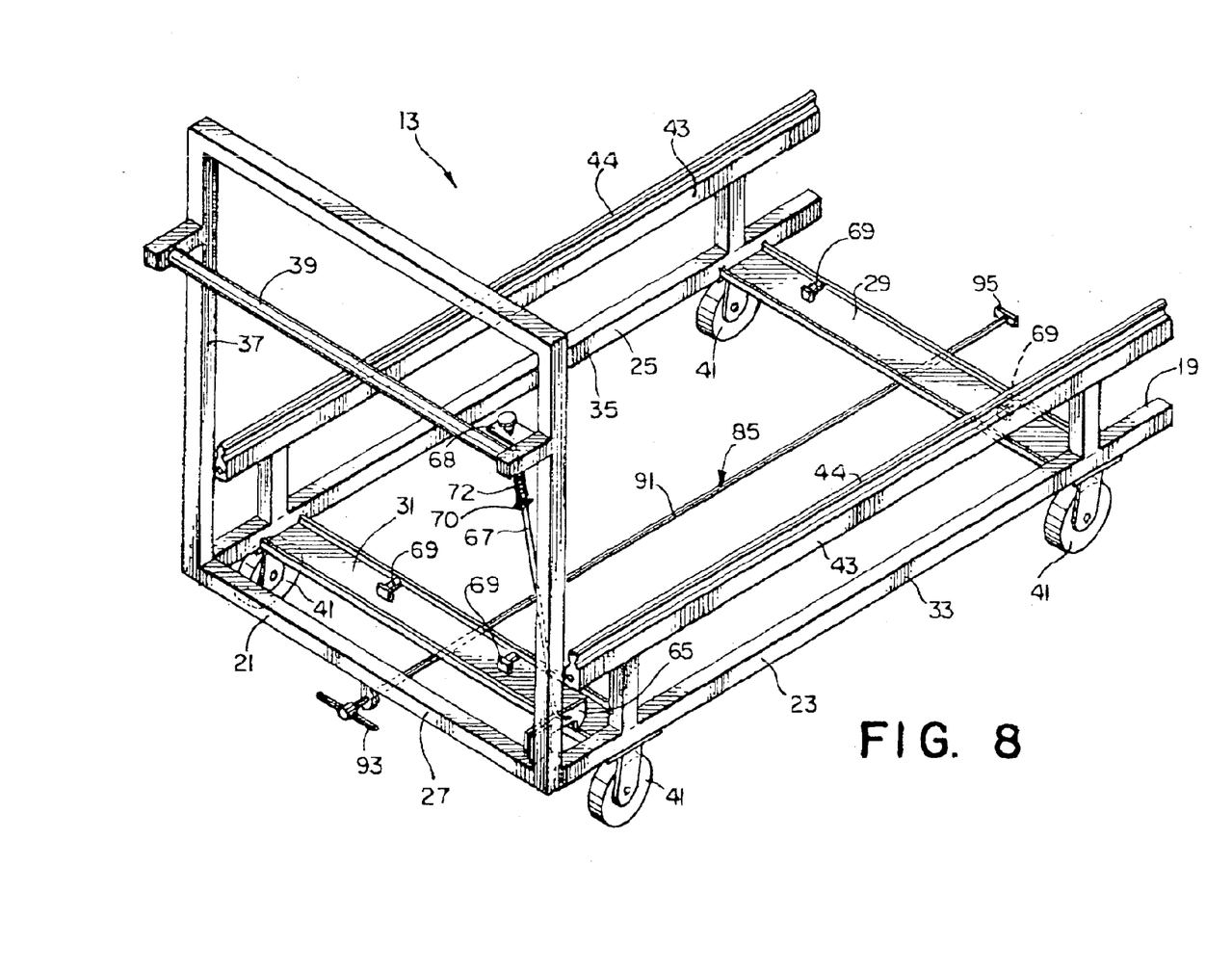
FIG. 8 is a view in perspective of the cart of FIG. 2.

As shown in FIGS. 1–8, and particularly in FIG. 8, the cart 13 for carrying the removable bin 15 has a front end portion 19, a rear end portion 21, and two side end portions 23, 25. The cart 13 has a U-shaped base frame portion 27 and a pair of cross members 29 & 31 extending between the leg portions 33, 35 of the base frame portion 27. The cart 13 also includes a handle support frame portion 37 extending upwardly from the base frame portion 27 at the rear end portion of the cart 13, and a handle assembly 39 is mounted onto the handle support frame portion 37 to facilitate pushing of the cart 13. Preferably, the cart 13 is constructed of aluminum alloy to reduce weight, and is anodized to provide a corrosion resistant surface that is easily cleaned.

Wheels 41, preferably castor wheels, are mounted on the underside of the base frame portion 27 of the cart 13 to provide mobility to the cart 13. Preferably, the wheels 41 are 5" diameter casters with polyethylene wheels, so as to provide smooth handling over various surfaces and to not mark or damage finished flooring.

A rail assembly 43 is provided on each leg portion 33, 35 of base frame portion 27 of the cart 13, and each rail assembly 43 has a rail 44.

As shown in the drawings, and particularly in FIGS. 12–16, the bin 15 has a bottom wall 45, and a front wall 47, a rear wall 49, and two side walls 51, 53 extending upwardly the bottom wall 45. Preferably the bin 15 is fabricated from corrosion resistant stainless steel and has a 33⅞ inch width, a 59 inch length, and a 36 inch height. A drain valve 55, preferably a ½ inch ball valve, is connected to the rear wall 49 of the bin 15 for permitting liquid to drain from the bin 15 when desired.

Figure 4:
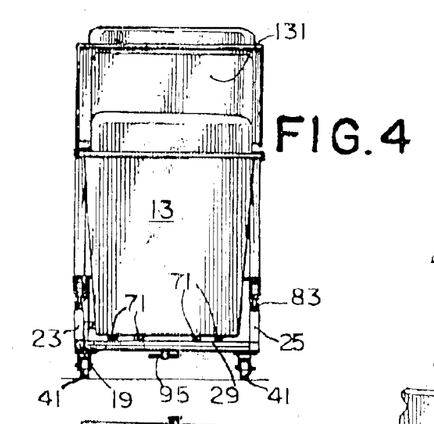
FIG. 4 is a view in front elevation of the cart and the bin of FIG. 2.
Figure 5:
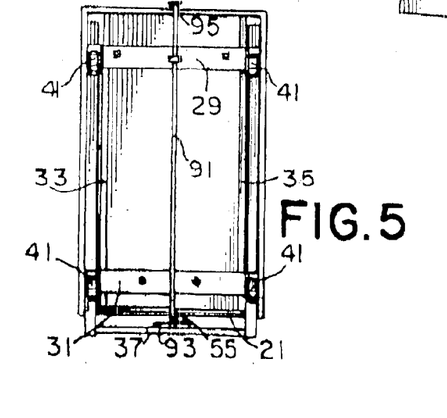
FIG. 5 is a bottom plan view of the cart and the bin of FIG. 2.
Figure 6:
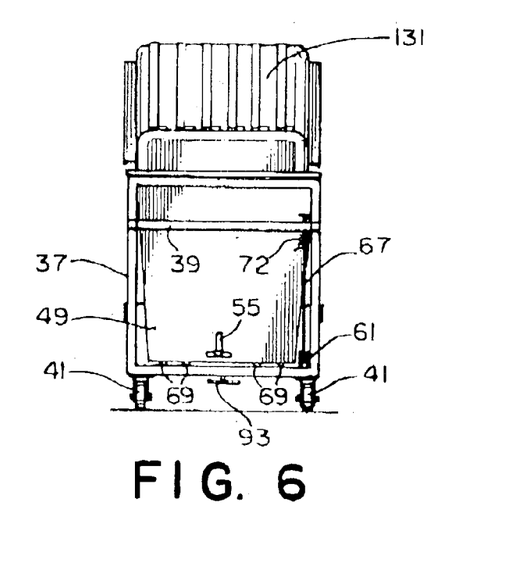
FIG. 6 is a view in rear elevation of the cart and the bin of FIG. 2.
Figure 7:
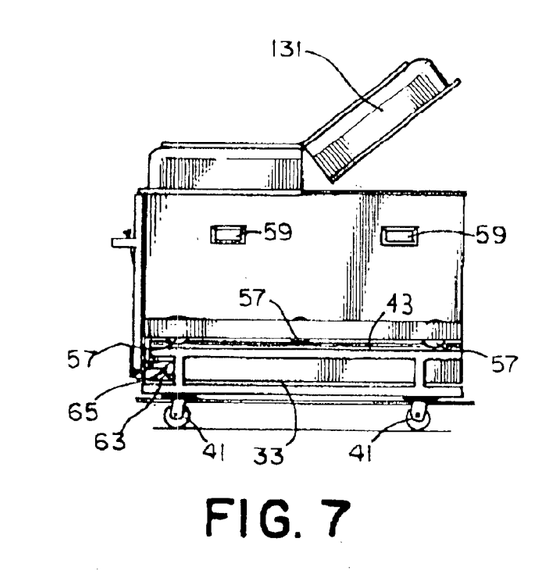
FIG. 7 is a view in side elevation showing the right side of the cart and bin of FIG. 2, with a partial cutaway to show a drain valve in the rear wall of the bin.

The bin 15 is provided with wheels 57 mounted on each side wall 51, 53 of the bin 15. The wheels 57 are spaced such that the wheels 57 engage the rail assemblies 43 located on the side end portions 23 and 25 of the cart 13 so that the bin 15 may be rolled off the cart 13 along the rails 44 when the bin 15 is being loaded into the sterilization chamber 17 from the cart 13 and so that the bin 15 may be rolled onto the cart 13 along the rails 44 and 80 when the bin 15 is being loaded onto the cart 13 from the sterilization chamber 17 after sterilization. Wheels 57 may be V-grooved to facilitate engagement on the rails 44, or, as shown in FIG. 4, the wheels 57 may be V-grooved along one of the side walls 51 and 53 and flat along the other of side walls 51 and 53 to facilitate alignment of the bin 15 with the rail assembly 79 of the sterilization chamber 17.

Figure 12:
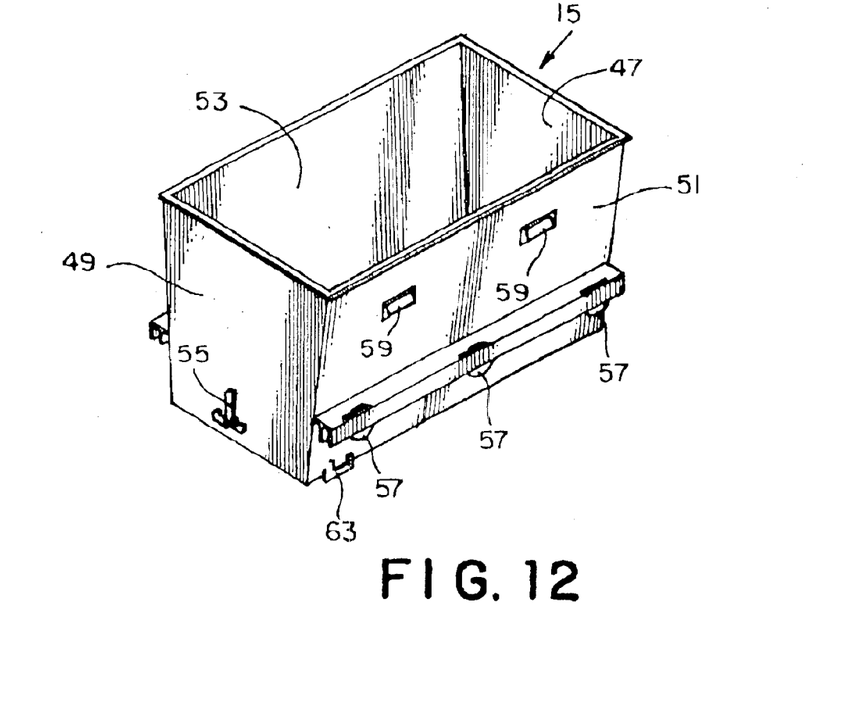
FIG. 12 is a view perspective of the bin of FIG. 2.
Figure 13:
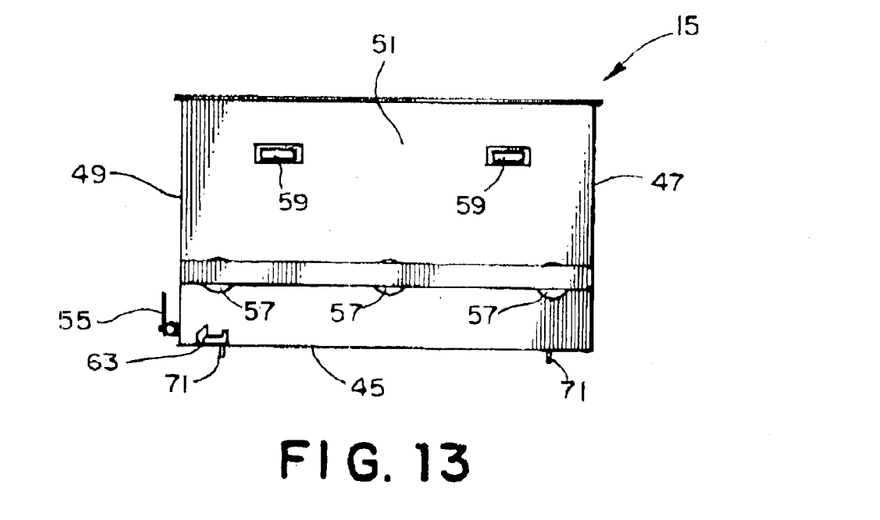
FIG. 13 is a view in side elevation showing the right side of the bin of FIG. 2.
Figure 14:
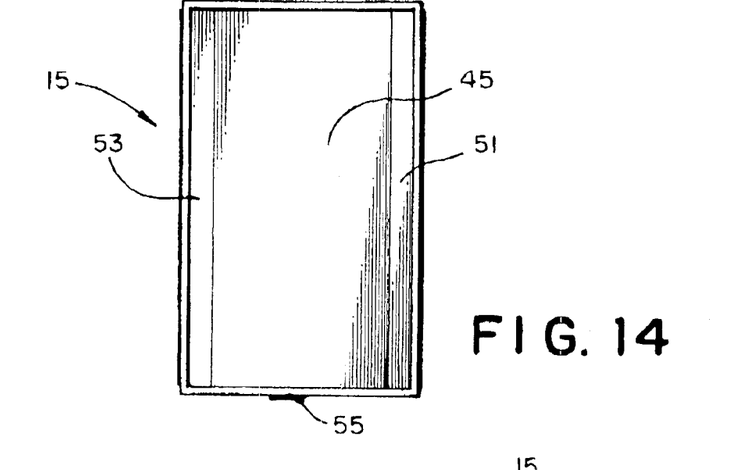
FIG. 14 is a view in top plan of the bin of FIG. 2.
Figure 15:
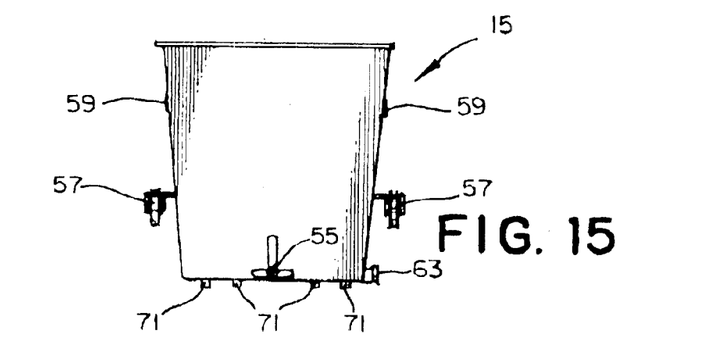
FIG. 15 is a view in rear elevation of the bin of FIG. 2.
Figure 16:
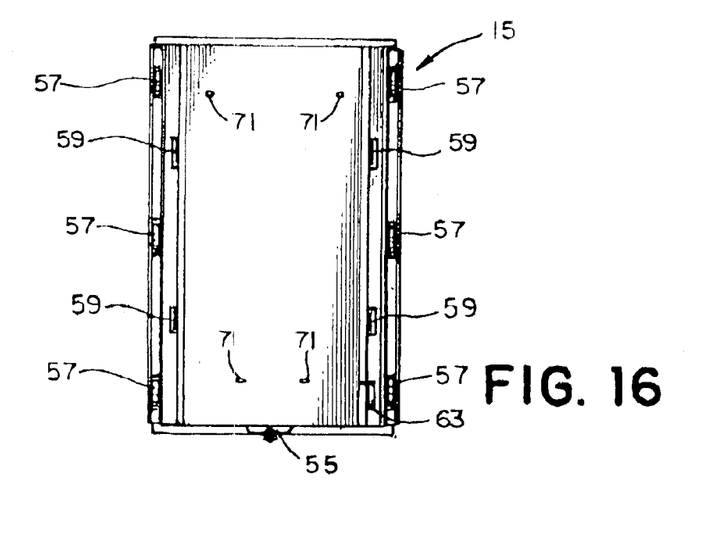
FIG. 16 is a view in bottom plan of the bin of FIG. 2.

Handle grips 59 are formed in the side walls 51, 53 of the bin 15 to facilitate handling of the bin 15.

Figure 17:
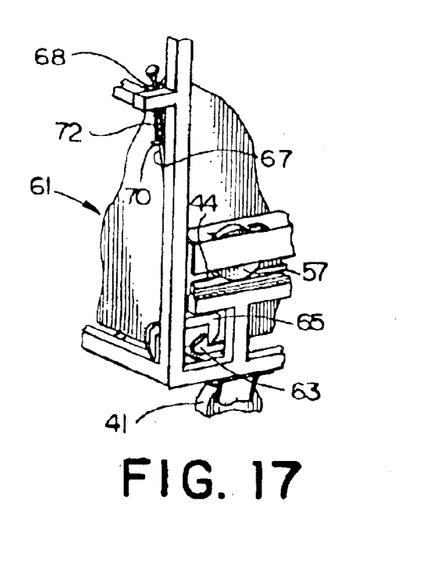
FIG. 17 is a view in perspective of a latching assembly for latching the bin of the invention to the cart of the invention.

As shown in detail in FIG. 17, a latching assembly 61 is provided for latching the bin 15 to the cart 13, when desired. The latching assembly 61 includes a catch member 63 mounted on the bin 15. The latching assembly 61 also has a hook arm 65 pivotally mounted on the cart 13 for engaging the catch member 63 when the bin 15 is positioned on the cart 13, to prevent the bin 15 from moving forward on the rail assemblies 43 of the cart 13 when it is desired to have the bin 15 secured to cart 13. A release rod 67 is connected to the hook arm 65 and may be pulled to disengage the hook arm 65 from the catch member 63 when it is desired to roll the bin 15 off of the cart 13. The upper end of the rod 67 extends through a hole in a plate 68 formed on the handle support frame portion 37. The upper end portion of the rod 67 also has a pin 70 extending through it, and a spring 72, which is mounted on the rod 68 between the pin 70 and the plate 68, biases the rod 67 and the hook arm 65 attached to the rod 67 downwardly into engagement with the catch member 63.

Figure 18:
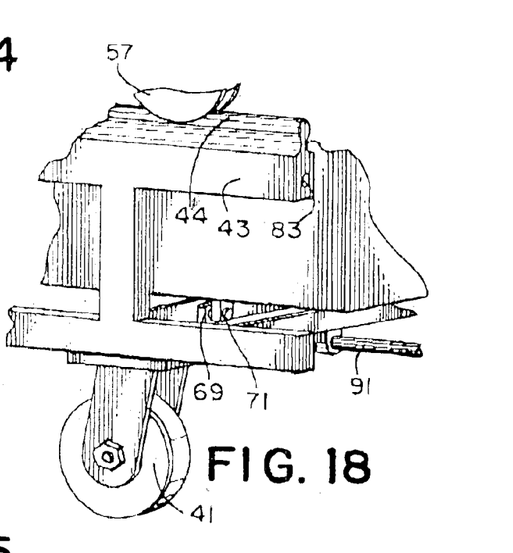
FIG. 18 is a view in perspective illustrating a locking pin formed on the cart being engaged by a bin locking tab formed on the bottom wall of the bin of the invention.

As shown in the drawings, and particularly in FIG. 18, the cart 13 also is provided with locking pins 69 formed on the cross members 29 and 31 that are received by bin locking tabs 71 formed on the bottom wall 45 of the bin 15 when the bin 15 is completely rolled onto the cart 13 to secure the bin 15 on the cart 13. The locking pins 69 when engaged by the bin locking tabs 71 block the bin 15 from falling off the side end portions 23 and 25 of the cart 13 or from being lifted off of the cart 13 or from falling off the cart 13 when the bin contents are dumped.

Figure 10:
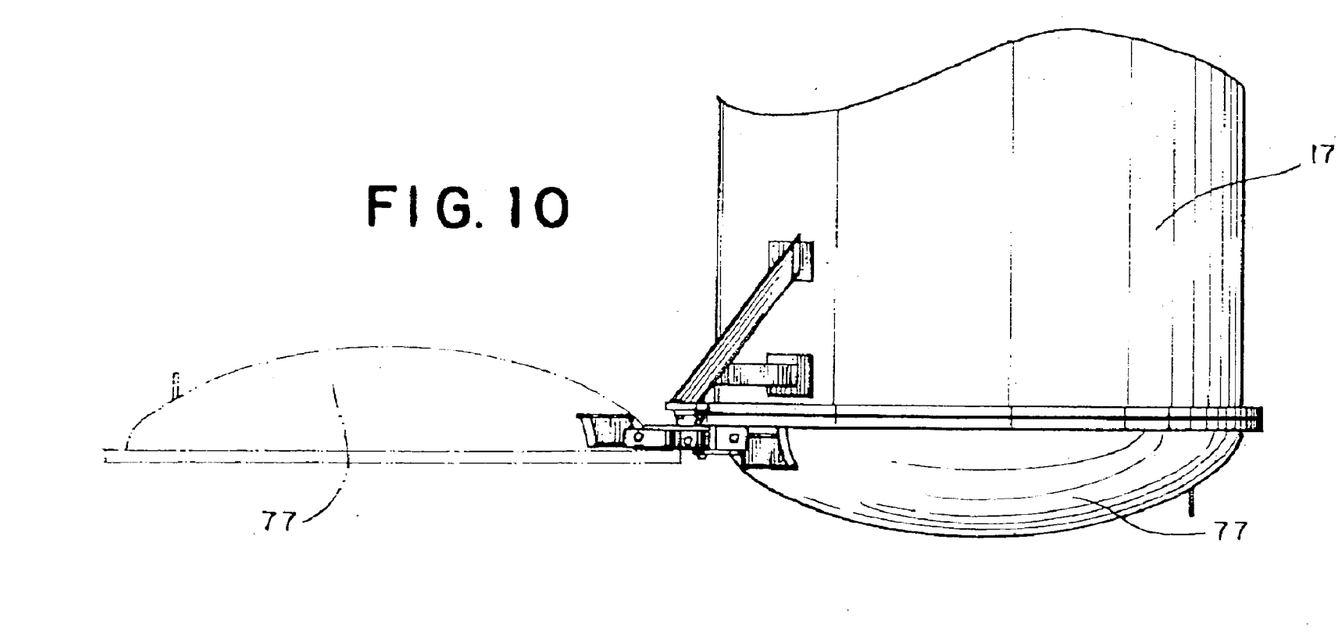
FIG. 10 is a partial view in top plan of the sterilization chamber illustrating the chamber door in opened and closed positions.

The sterilization chamber 17 has in interior 73 where sterilization takes place. The sterilization chamber 17 has an opening 75 through which access to the interior 73 of the sterilization chamber 17 is obtained, and the sterilization chamber 17 has a door 77 mounted at the opening 75 for sealingly closing the opening 75 against both pressure and vacuum when closed. The sterilization chamber 17 preferably is 60 inches in diameter and 64 inches long, and is constructed of corrosion resistant stainless steel. It is mounted on chamber support cradles and positioned at a convenient elevation for use in conjunction with the cart 13 and bin 15. As shown in FIG. 10, the door 77 preferably is a full opening hinged door that provides unobstructed access to the sterilization chamber 17 when the door 77 is fully opened. The door 77 preferably is equipped with an automatic latching mechanism to seal the door against both pressure and vacuum. Also, the door 77 preferably is equipped with safety innerlocks to prevent opening the door until safe pressure and temperature conditions are restored.

Preferably, the sterilization chamber 17 is equipped with a pressure relief valve device to prevent over pressurization, and preferably, the sterilization chamber 17 is designed and constructed in accordance with the ASME Code Sections VIII, Division 1, and may receive an ASME "U" stamp as an unfired pressure vessel.

Figure 1:
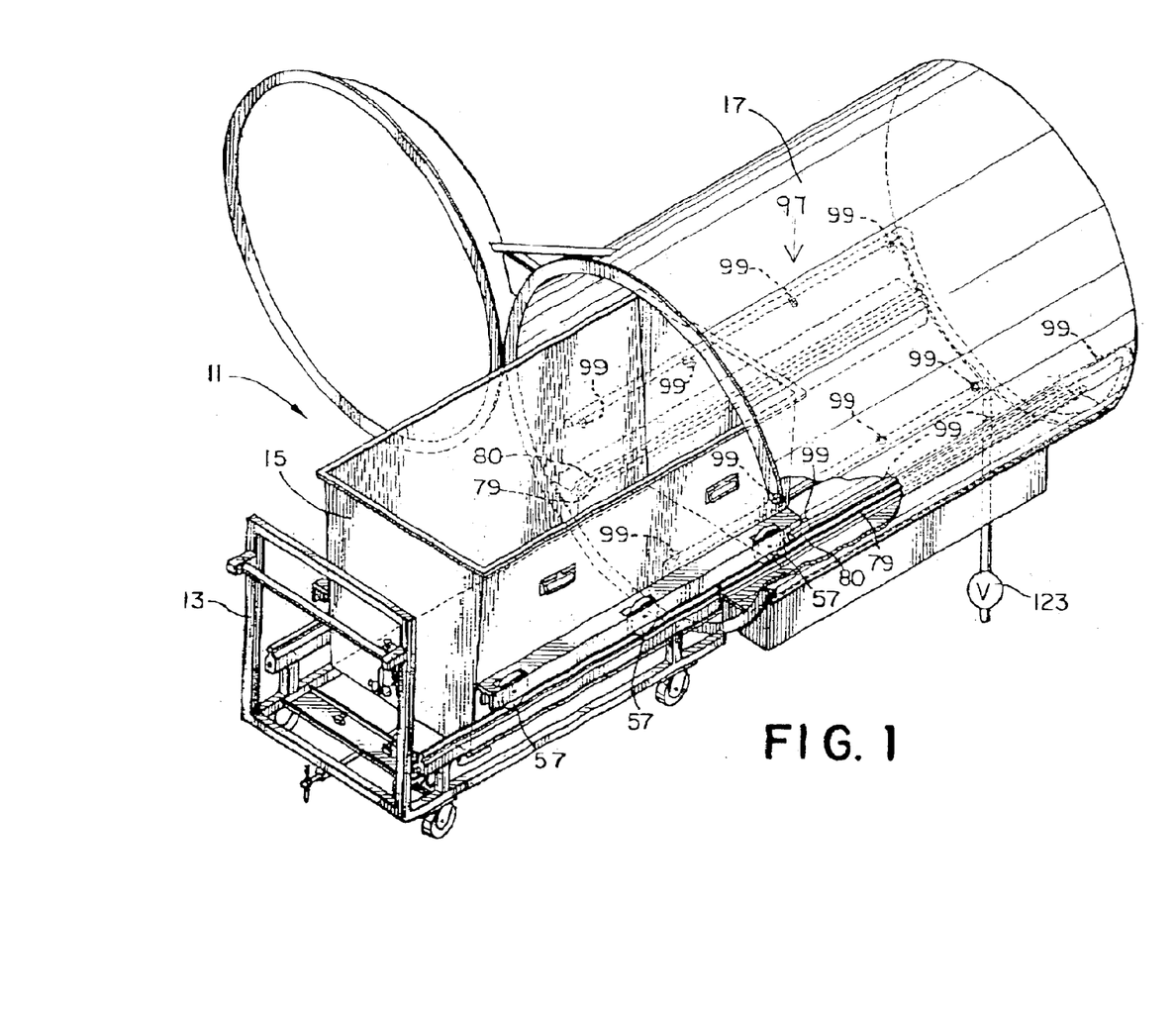
FIG. 1 is a view in perspective of a steam sterilization system constructed in accordance with the invention, showing a removable bin for holding items (such as medical waste) to be sterilized being rolled from a cart which has been attached to a sterilization chamber, into the sterilization chamber for commencement of a sterilization process to sterilize the items to be sterilized in accordance with the invention.
Figure 2:
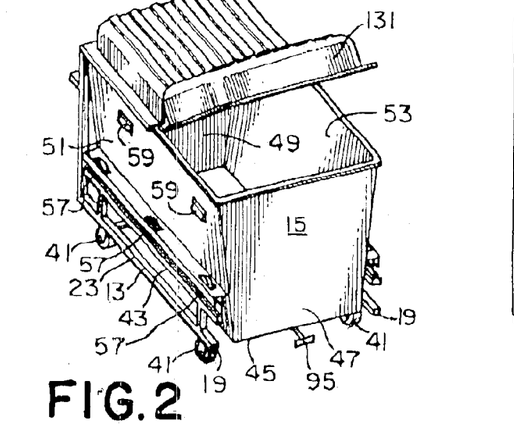
FIG. 2 is a view in perspective of a cart having the "removable" bin mounted thereon, which are constructed with the invention.
Figure 3:
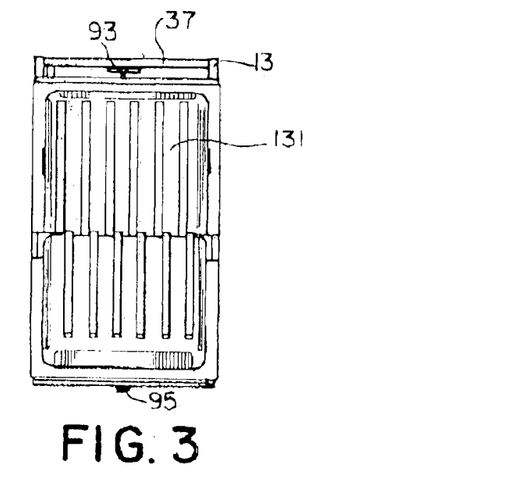
FIG. 3 is a view in top plan of the cart and the bin of FIG. 2.
Figure 9:
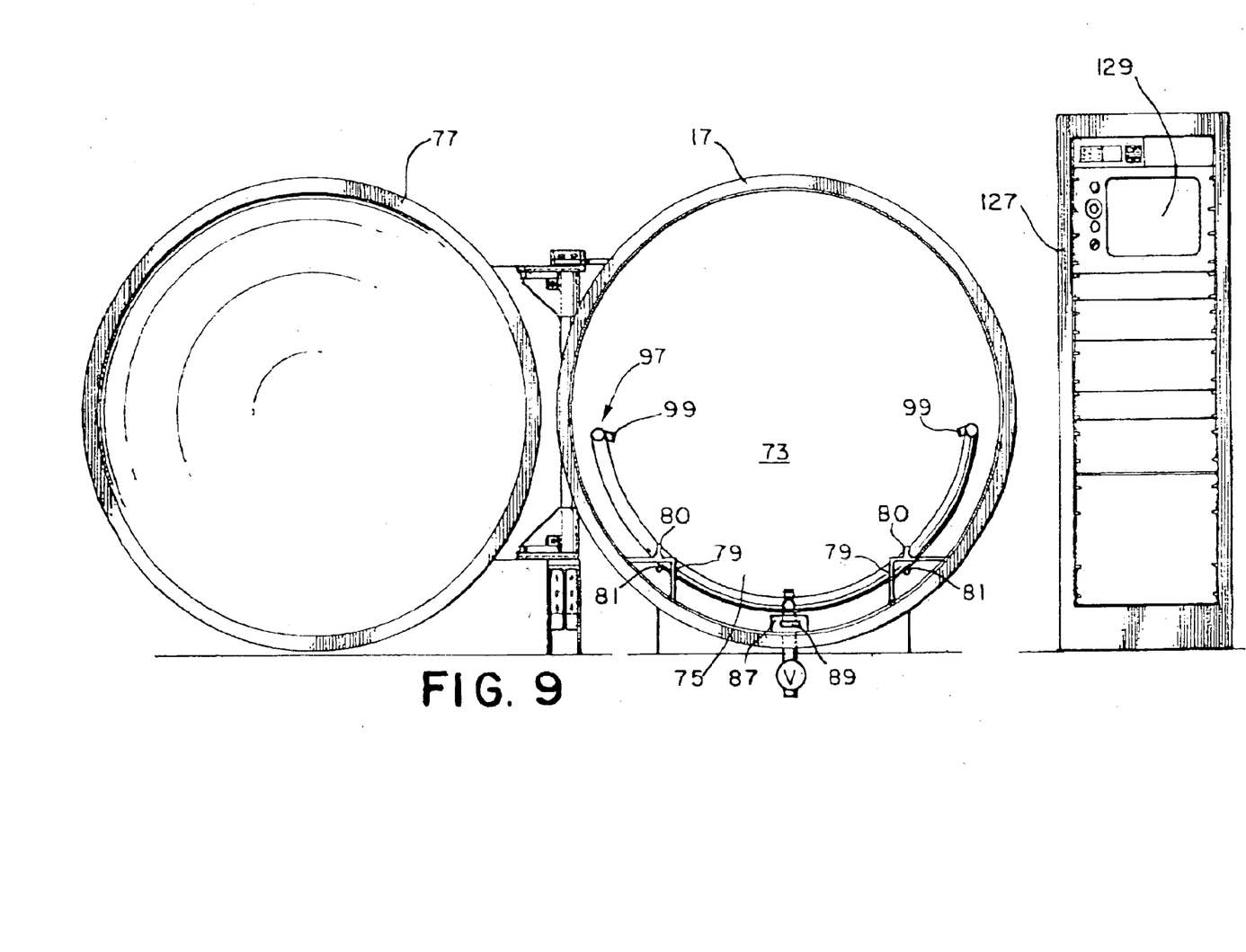
FIG. 9 is a view in front elevation showing a sterilization chamber with its door being opened, and a controller for the sterilization system.

As shown in FIGS. 1 and 9, the sterilization chamber 17 is provided with a rail assembly 79 that is located in the interior 73 of the sterilization chamber 17. The rail assembly 79 has pair of parallelly spaced rails 80 on which the wheels 57 of the bin 15 ride when the bin 15 is inserted into the sterilization chamber 17 from the cart 13 prior to sterilization and on which the wheels 57 of the bin 15 ride when the bin 15 is being removed from the sterilization chamber 17 and rolled back onto the cart 13 via rail assemblies 43 after sterilization.

A pair of alignment pins 81 (FIG. 9) are mounted on the sterilization chamber 17 at the opening 75 to the sterilization chamber 17, which are received in a pair of pin receivers or bores 83 (FIGS. 4 and 18) formed in the front end portion 19 of the cart 13 when the cart 13 is properly aligned with the sterilization chamber 17 to permit the bin 15 to be rolled off the cart 13 along the rail assemblies 43 of the cart 13 and into the interior 73 of the sterilization chamber 17 along the rail assemblies 79 of the sterilization chamber 17.

A locking assembly 85 is provided for locking the cart 13 to the sterilization chamber 17 at the chamber opening 75 when the bin 15 is to be moved from the cart 13 to the interior 73 of the sterilization chamber 17 or when the bin 15 is to be moved from the interior 73 of the sterilization chamber 17 to the cart 13. As shown in FIG. 9, the locking assembly 85 has an attachment plate 87 mounted on the sterilization chamber 17 near the chamber opening 75, and the attachment plate 87 has a slot 89 formed therein. As shown in FIGS. 8 and 18, a shaft 91 is rotatably mounted on the underside of the cart 13. A handle 93 is positioned at the first end portion of the shaft 91 for rotating the shaft 91, and a cross member 95 is located at the second end portion of the shaft 91 and is sized to fit through the slot 89 formed in the attachment plate 87 when the cross member 95 is aligned with the slot 89. The cross member 95 is sized not to fit back through the slot 89 in the attachment plate 87 when the shaft 91 is rotated to position the cross member 95 out of alignment with the slot 89.

As shown in FIGS. 1 and 9, a water spraying assembly 97 is provided to the sterilization chamber 17 for cooling the bin 15 after sterilization and prior to removal of the bin 15 from the sterilization chamber 17. The water spraying assembly 97 includes nozzles 99 mounted in the interior 73 of the sterilization chamber 17 that are aligned to spray cooling water on the outside of the walls 45, 47, 49, 51 and 53. In the preferred embodiment of the invention shown in the drawings, twelve nozzles 99 are provided. The nozzles 99 spray water to cool down the bin 15 after sterilization has occurred and are arranged to do so by spraying the outside of the walls of the bin 15. The nozzles 99 are arranged so as not to get water on the treated, sterilized waste held in the bin 15.

Figure 11:
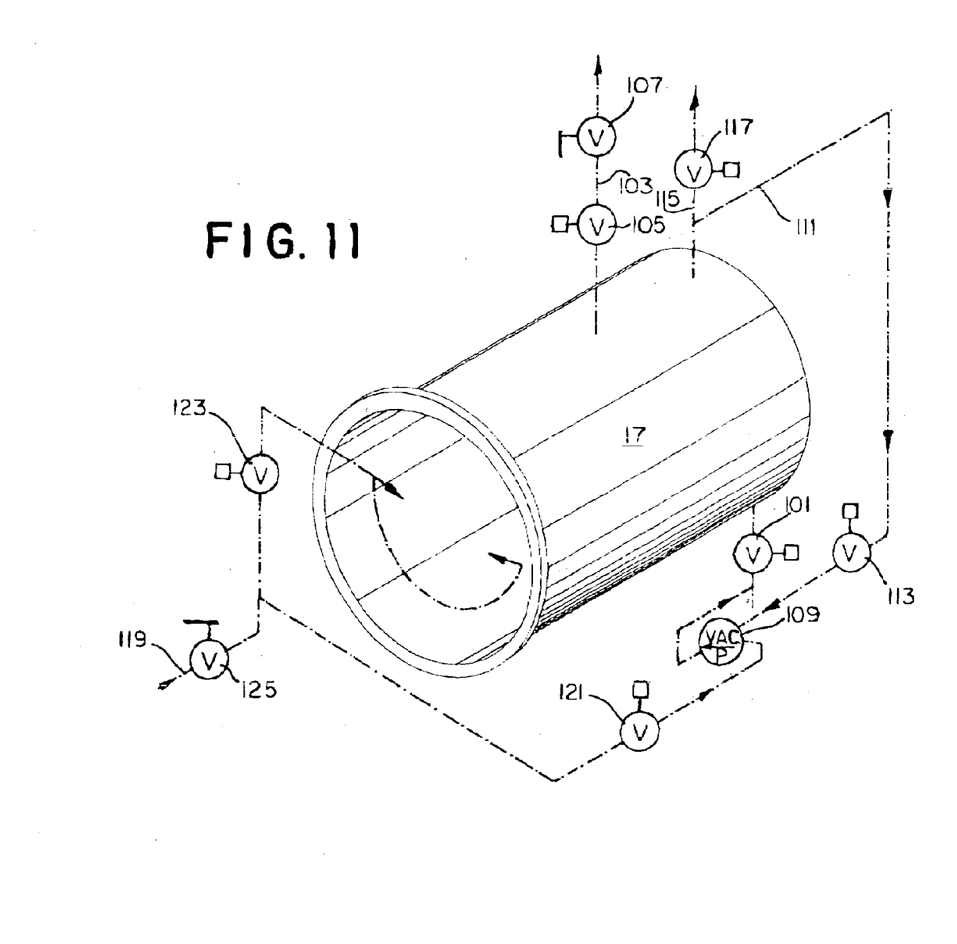
FIG. 11 is a schematic drawing illustrating the steam, vacuum, and water systems used in conjunction with the sterilization system of the invention.

A drain valve 101 is connected to the sterilization chamber 17 for liquid to drain from the sterilization chamber 17 when desired.

As shown schematically in FIG. 11, piping 103, preferably a 2-inch diameter line, is provided to supply steam, preferably at 15 to 20 psig, to the sterilization chamber 17. A solenoid controlled steam valve 105 is provided along the piping 103 to control the flow of steam into the sterilization chamber 17. Preferably, a manual isolation valve 107, preferably a manual ball valve, is provided along the piping 103 upstream from the solenoid steam control valve 105 as a safety feature. When the sterilization system 11 is not in use, the isolation valve 107 may be manually closed to prevent steam from accidentally flowing into the sterilization chamber 17 if the steam valve 105 opens.

A vacuum pump 109 is provided for evacuating the sterilization chamber 17 between steam cycles during the sterilization process. The vacuum pump 109 is provided along piping 111. Preferably, the vacuum pump 109 is a single stage, liquid ring pump that uses water as the seal fluid and that is suited as a vapor pump. The vacuum pump 109 preferably is connected to the sterilization chamber 17 through a stainless steel manifold and is isolated by a solenoid-activated vacuum valve 113. The preferred performance specifications for the vacuum pump 109 are:

Pumping speed: 300 cfm

Base pressure: 28 in-Hg

Time to vacuum: <5 minutes

Motor: 20 HP

Piping 111 includes a vent portion 115 for venting the sterilization chamber 17 to atmosphere, and a valve 117, preferably an electromagnetic solenoid activated valve, is provided along piping vent portion 115 to open and close the vent portion 115.

Piping 119, preferably a ¾ inch diameter line, is provided to supply water, preferably at 30 psig minimum, to the vacuum pump 109 and to the water spray assembly 97. A valve 121, preferably an electro-magnetic solenoid valve, is provided along the piping 119 to control flow of water (to be used as seal fluid) to the vacuum pump 109.

A valve 123, preferably an electromagnetic solenoid activated valve, is provided along the piping 119 to control the flow of water to the water spray assembly 97.

An isolation valve 125, preferably a manual ball valve, is provided along piping 119 upstream of both the valve 121 and the valve 123 as a safety feature to be manually closed when the sterilization system 11 is not in use.

Referring to FIG. 9, a programmable logic controller 127 manages sequential control functions and system interlocks. The controller 127 controls the steam valve 105, vent valve 117, the drain valve 101, the liquid ring and water supply valve 121, the cooling spray valve 123, and the vacuum pump 109, and it monitors process temperature and pressure. The controller 127 is preferably housed in a weather-proof NEMA enclosure.

Preferably, a chart recorder 129 is provided to monitor time, temperature, and pressure, and to provide a permanent record for quality control documentation.

As shown in FIGS. 2–4 and 6–7, a removable lid 131 is provided for covering the bin 15. Preferably, the removable lid 131 is made of light-weight plastic and is hinged to provide easy access to the bin 15 without requiring removal of the entire lid 131 from the bin 15 prior to sterilization. The entire lid 131 is removed prior to the bin 15 being rolled into the sterilization chamber 17 during the sterilization process.

In operation, the cart 13 having the bin 15 secured thereon is used to collect regulated medical waste to be sterilized. The regulated medical waste that is to be sterilized is placed in the bin 15. The lid 131 is preferably used to cover the bin 15 and the medical waste contained therein prior to sterilization. The preferred hinged lid 131 shown in the drawings facilitates access to the bin 15 for placement of medical waste therein.

After the medical waste has been collected, the cart 13 with the bin 15 mounted thereon is moved to the sterilization chamber 17, where the lid 131 is removed from the bin 15 and placed aside.

The door 79 of the sterilization chamber 17 is opened and the cart 13 is pushed to the opening 75 of the sterilization chamber 17 so that the alignment pins 81 mounted on the sterilization chamber 17 at the opening of 75 of the sterilization chamber 17 are inserted into the pin receivers 83 on the cart 13 to assure that the cart 13 is properly aligned with the opening 75 of the sterilization chamber 17, thereby aligning the rail assemblies 43 of the cart 13 with the rail assemblies 79 of the sterilization chamber 17.

While the cart 13 is being pushed up against the sterilization chamber 17 with the pin receivers 83 receiving the alignment pins 81, the cross member 95 is positioned to pass through the slot 89 in the attachment plate 87, and after the cross member 95 has been inserted through slot 89, the cross member 95 is positioned by rotation of the shaft 91 using handle 93 to be out of alignment with the slot 89 such that the attachment plate 87 blocks the cross member 95 from moving back out of the slot 89, thereby locking the cart 13 to the sterilization chamber 17 preventing rearward movement of the cart 13 away from the sterilization chamber 17.

Next, the release rod 67 is pulled to disengage the hook arm 65 from the catch member 63 to permit the bin 15 to roll forward on the rail assemblies 43. After the latching assembly 61 has been disengaged, the bin 15 is rolled on its wheels 57 from the cart 13 into the interior 73 of the sterilization chamber 17 along the aligned rail assemblies 43 and 79.

Once the bin 15 has been rolled into the sterilization chamber 17, the cart 13 is unlocked from the sterilization chamber 17 by rotating the shaft 91 to position the cross member 95 in alignment with the slot 89 of the attachment plate 87, and then the cart 13 is rolled away from the sterilization chamber 17.

Then, the drain valve 55 of the bin 15 is opened and the door 77 of the sterilization chamber 17 is closed.

The start button on the controller 127 is then pressed to start the sterilization process. First, the controller 127 opens the steam valve 105 to permit steam to fill the sterilization chamber 17. The controller 127 closes the vent valve 117 and the drain valve 101 of the sterilization chamber 17 when the sterilization chamber 17 is full of steam. Prior to the closing of the vent valve 117 and the drain valve 101, the air in the sterilization chamber 17 outside the waste container systems (i.e., sharps containers, sealed red plastic bags, etc.) is "gravity" displaced by the steam being fed into the sterilization chamber 17.

A thermocouple is mounted in the interior 73 of the sterilization chamber 17 and is connected to the controller 127 to indicate the temperature inside the interior 73 of the sterilization chamber 17. After 250° Fahrenheit is reach within the interior 73 of the sterilization chamber 17, the controller 127 initiates a hold period to kill all airborne pathogens in the containment systems. Preferably, the hold period is about 5 minutes, but can be adjusted to various time lengths based on the pathogen load factor.

With the vent valve 117 closed, controller 127 closes the steam valve 105 and then drains valve 101 is cycled open until the pressure in the sterilization chamber 17 goes to zero gauge pressure. The drain valve 101 is then closed. Valves 121 and 113 are opened and vacuum pump 109 is initiated to draw a vacuum in the sterilization chamber 17 to remove the now sterilized air from the containment systems.

After creating a vacuum withdrawing the air from within the containment system, the vacuum pump 109 is stopped and the associated valves 113 and 121 are closed. The steam valve 105 is then opened admitting high temperature, high pressure steam commencing the waste sterilization cycle. After a preferred retention period of one (1) hour at or above 250° Fahrenheit (or longer if required by the location, state's regulations etc.), the steam valve 105 is closed. The drain valve 101 then is cycled open until the chamber pressure goes to zero gauge pressure. The drain valve 101 is then closed.

Next, valves 113 and 121 are opened and vacuum pump 109 is initiated to draw a vacuum to flash off the condensate on the waste to dry it. After the condensate has evaporated and the waste is dry, the vacuum pump 109 is shut off and the valves 113 and 121 are closed. The vent valve 113 and the drain valve 101 are then opened.

At this point, the cart 13 has a temperature of approximately 212° Fahrenheit. To cool the cart to room temperature, valve 123 is opened to let cooling water flow to and through the water spray assembly 97 to spray cooling water on the outside of the walls 45, 47, 49, 51 and 53 of the bin 15 to cool down the bin 15. Upon the bin 15 reaching room temperature, valve 123 is closed. At this point, the controller 127 signals, preferably by initiating a green light located on the door 77 of the sterilization chamber 17, that the door 77 may be opened and the bin 15 removed from the sterilization chamber 17.

The door 77 is then opened, the drain valve 55 of the bin 15 is closed, and the cart 13 is again located adjacent to the opening 75 of the sterilization chamber 17 with the alignment pins 81 being received by the pin receivers 83 to assure proper alignment of the cart 13 with the sterilization chamber 17, and with the cart 13 locked to the sterilization chamber 17 using the locking assembly 85.

With the cart 13 aligned properly and locked in place to the sterilization chamber 17, the bin 15 containing the sterilized waste may be rolled from the interior 73 of the sterilization chamber 17 onto the cart 13 along the rail assemblies 43 and 79. As the bin 15 rolls fully onto the cart 13, the locking pins 69 of the cart 13 are received in the bin locking tabs 71 of the bin 15, and the hook arm 65 may be positioned to engage the catch member 63, thereby securing the bin IS onto the cart 13.

With the bin 15 secured on the cart 13, the cart 13 may be unlocked from the sterilization chamber 17 by rotating the shaft 91 to position the cross member 95 in alignment with the slot 89 in the attachment plate 87, thereby permitting the cart 13 to be pulled away from the sterilization chamber 17.

The cart 13 with the bin 15 mounted thereon may be moved to a dump location where the sterilized waste may be dumped into a compactor.

The lid 131 may now be replaced onto the bin 15. The cart 13 with the bin 15 mounted thereon is now ready to be used to gather more medical waste for sterilization.

As is detailed above, the inventive sterilization process uses a combination of steam injection and vacuum to treat potential airborne pathogens, to enhance heat transfer, a to increase system efficacy. The use of vacuum removes residual air and provides and transport mechanism for steam delivery. Sterilization is accomplished using steam at a pressure of 15 psig, which corresponds to an operating temperature of 250° Fahrenheit.

An important characteristic of my inventive sterilization system 11 is management of airborne pathogens. The sterilization process cycle begins by gravity charging the sterilization chamber 17 with steam, thereby increasing the temperature to the killing temperature for airborne pathogens, then subsequently removing the air from the waste containment systems (i.e., sharps containers, sealed red plastic bags, etc.) which kills airborne pathogens that might otherwise be released through the discharge of the vacuum pump 109.

The sterilization system 11 is preferably used with medical waste containment systems having ventilation means formed therein. Venting the containment systems allows steam to permeate confined volumes of the containment systems and accelerates the heating cycle.

My sterilization system 11 provides a material handling system that accommodates the complete cycle of the processing medical waste, including the collection of medical waste, sterilization of the medical waste, and the transportation and dumping of the treated medical waste from the sterilization unit to the treated sterilized waste facility compactor. The handling system eliminates the need to transfer waste products from a collection cart to the sterilizer, thereby improving pathogen containment. Further, the handling system eliminates the need to transfer treated sterilized waste product from the sterilizer to the plastic/rubber carts for transportation to the hospital's compactor.

The material handling system provided by my invention reduces physical handling of the waste material by hospital personnel thereby reducing the chances of injury to hospital personnel since the waste material need not be physically handled by hospital personnel after it is initially loaded into the bin 15.

What is claimed is:

1. A steam sterilization system for sterilizing medical waste, comprising a cart, the cart having a front end portion, a rear end portion, and two side end portions, the cart having wheels mounted thereon to provide mobility to the cart, and the cart having a rail assembly positioned at each side end portion, a bin for holding medical waste, the bin being removably mountable to the cart, the bin having a bottom wall, and a front wall, a rear wall, and two side walls extending upwardly from the bottom wall, the bin having wheels mounted on each side wall of the bin and spaced such that the wheels engage the rail assemblies of the cart when the bin is being loaded onto the cart and such that the wheels engage the rail assemblies of the cart when the bin is being removed from the cart, and a sterilization chamber, the chamber having an interior, the chamber having an opening through which access to the interior of the chamber is obtained, and the chamber having the door mounted at the opening for sealingly closing the opening against both pressure and vacuum when closed, the chamber having a rail assembly mounted in the interior of the chamber on which the wheels of the bin ride when the bin is inserted into the chamber from the cart prior to sterilization and on which the wheels of the bin ride when the bin is being removed from the chamber and rolled back onto the cart after sterilization, a steam valve connected to the chamber for introducing steam when desired into the chamber, and a vacuum pump connected to the chamber for evacuating air in the chamber when desired.

2. The sterilization system of claim 1, the wheels of the cart being caster wheels.

3. The sterilization system of claim 1, further including a latching assembly for latching the bin to the cart, the latching assembly including a catch member mounted on the bin, a hook arm pivotily mounted on the cart for engaging the catch member to prevent the bin from moving forward on the rail assemblies of the cart when it is desired to have the bin secured to the cart, and a release rod mounted on the hook arm for disengaging the hook arm from the catch member when it is desired to roll the bin off of the cart.

4. The sterilization system of claim 1, the cart having a handle formed thereon for facilitating handling of the cart.

5. The sterilization system of claim 1, the cart having a locking pin formed thereon, and the bin having a bin locking tab formed on its bottom wall for receiving the locking pin when the bin is rolled on the cart to secure the bin on the cart.

6. The sterilization system of claim 1, further including an alignment pin mounted on the sterilization chamber at the chamber opening, and a pin receiver formed in the front end portion of the cart for receiving the alignment pin when the cart is aligned properly with the chamber to permit the bin to be rolled off the cart along the rail assemblies of the cart and into the interior of the chamber along the rail assembly of the chamber.

7. The sterilization system of claim 1, further including a locking assembly for locking the cart to the chamber at the chamber opening when the bin is to be moved from the cart to the interior of the chamber or when the bin is to be moved from the interior of the chamber to the cart, the locking assembly having an attachment plate mounted on the chamber near the chamber opening, the attachment plate having a slot formed therein, a shaft rotatably mounted on the cart, a handle at a first end portion of the shaft for rotating the shaft, and a cross member formed on a second end portion of the shaft and sized to fit through the slot formed in the attachment plate when the cross member is aligned with the slot and sized not to fit back through the slot in the attachment plate when the shaft is rotated to position the cross member of the locking assembly out of alignment with the slot.

8. The sterilization system of claim 1, further including a drain valve connected to the bottom wall of the bin for permitting liquid to drain from the bin when desired.

9. The sterilization system of claim 1, further including handle grips formed in the side walls of the bin to facilitate handling of the bin.

10. The sterilization system of claim 1, further including a removable lid for covering the bin.

11. The sterilization system of claim 1, further including a water spraying assembly for cooling the bin after sterilization, the water spraying assembly having nozzles mounted in the interior of the chamber and aligned to spray cooling water on the outside of the walls of the bin.

12. The sterilization system of claim 1, further including a drain valve connected to the chamber to permit liquid to drain from the chamber when desired.

13. A sterilization system, comprising a cart, the cart having a front end portion, a rear end portion, and two side end portions, the cart having wheels mounted thereon to provide mobility to the cart, and the cart having a rail assembly positioned at each side end portion, a bin for holding items to be sterilized, the bin being removably mountable to the cart, the bin having a bottom wall, and a front wall, a rear wall, and two side walls extending upwardly from the bottom wall, the bin having wheels mounted on each side wall of the bin and spaced such that the wheels engage the rails of the cart when the bin is being loaded onto the cart and such that the wheels engage the rails of the cart when the bin is being removed from the cart, and a sterilization chamber, the chamber having an interior, the chamber having an opening through which access to the interior of the chamber is obtained, and the chamber having the door mounted at the opening for sealingly closing the opening when closed, the chamber having a rail assembly mounted in the interior of the chamber on which the wheels of the bin ride when the bin is inserted into the chamber from the cart prior to sterilization and on which the wheels of the bin ride when the bin is being removed from the chamber and rolled back onto the cart after sterilization.

14. A method of sterilizing medical waste contained in waste containment systems, comprising the steps of placing medical waste contained in waste containment systems into a sterilization chamber, displacing the air in the sterilization chamber with steam, heating the sterilization chamber with the steam to an effective temperature for killing all airborne pathogens in the waste containment systems and maintaining the temperature in the sterilization chamber at or above the effective temperature until the airborne pathogens are killed, drawing a vacuum in the sterilization chamber after the airborne pathogens in the containment systems have been killed, introducing steam into the sterilization chamber again, and heating the sterilization chamber with the steam to an effective temperature to sterilize the medical waste and maintaining the temperature in the sterilization chamber at or above the effective temperature until the medical waste is sterilized.

15. The method of claim 14, further including the step of drawing a vacuum in the sterilization chamber after the medical waste has been sterilized to flash off any condensate on the medical waste.

16. A method of collecting and sterilizing medical waste with the sterilization system of claim 13, comprising the steps of collecting medical waste to be sterilized in the bin removably mounted on the cart, transporting the medical waste to be sterilized using the cart with the bin removably mounted thereon to the sterilization chamber, connecting the cart to the sterilization chamber to secure the cart to the sterilization chamber and align the rail assemblies of the cart with the rail assembly of the sterilization chamber, disconnecting the bin from the cart, rolling the bin on its wheels from the cart into the sterilization chamber along the aligned rail assemblies, and sterilizing the medical waste contained within the bin in the sterilization chamber.

17. The method of claim 16, further including the step of rolling the bin on its wheels from the sterilization chamber onto the cart along the aligned rail assemblies after the medical waste has been sterilized, connecting the bin to the cart, and transporting the cart having the bin connected thereto to a dump location where the now sterilized medical waste may be dumped.

* * * * *